(12) United States Patent
LaPlaca

(10) Patent No.: US 8,479,742 B2
(45) Date of Patent: Jul. 9, 2013

(54) CONSTANT RATE DELIVERY DEVICE

(75) Inventor: Matthew LaPlaca, Cumberland, RI (US)

(73) Assignee: Hologic, Inc., Marlborough, MA (US)

( * ) Notice: Subject to any disclaimer, the term of this patent is extended or adjusted under 35 U.S.C. 154(b) by 166 days.

(21) Appl. No.: 13/036,686

(22) Filed: Feb. 28, 2011

(65) Prior Publication Data

US 2012/0216815 A1  Aug. 30, 2012

(51) Int. Cl.
*A61M 5/178* (2006.01)
*A61M 37/00* (2006.01)
*A61M 31/00* (2006.01)
*A61M 5/00* (2006.01)
*A61M 16/00* (2006.01)
*A61F 6/06* (2006.01)
*A61F 6/14* (2006.01)
*A61F 2/02* (2006.01)
*A61F 11/00* (2006.01)
*A61F 7/12* (2006.01)
*A61F 2/06* (2006.01)
*A61F 2/04* (2006.01)

(52) U.S. Cl.
USPC ............. 128/831; 128/207.14; 128/207.15; 128/207.16; 128/830; 128/832; 128/833; 128/834; 128/835; 128/836; 128/837; 128/838; 128/839; 128/840; 128/841; 623/1; 623/11; 623/23.66; 623/23.69; 623/23.7; 623/1.12; 623/1.15; 623/23.75; 623/1.23; 623/1.21; 606/151; 606/153; 606/155; 606/156; 606/191; 606/197; 606/199; 606/108; 606/198; 606/194; 606/192; 606/193; 606/200; 606/213; 604/8; 604/57; 604/59; 604/60; 604/95.05; 604/113; 604/164.03; 604/531

(58) Field of Classification Search
USPC .......... 128/207.14, 207.15, 207.16, 830–841; 623/1, 11, 12, 23.66, 23.69, 23.7, 1.12, 1.15, 623/23.75, 1.23, 1.21; 606/151, 153, 155, 606/156, 191, 197, 199, 108, 198, 194, 192, 606/193, 200, 213; 604/8, 57, 59, 60, 93.01, 604/95.05, 113, 164.03, 531
See application file for complete search history.

(56) References Cited

U.S. PATENT DOCUMENTS

| | | | |
|---|---|---|---|
| 5,095,917 A | 3/1992 | Vancaillie | |
| 5,681,572 A | 10/1997 | Seare, Jr. | |
| 5,840,061 A * | 11/1998 | Menne et al. | 604/68 |
| 5,954,715 A | 9/1999 | Harrington et al. | |
| 6,068,626 A | 5/2000 | Harrington et al. | |
| 6,287,275 B1 * | 9/2001 | Atala | 604/28 |
| 6,309,384 B1 | 10/2001 | Harrington et al. | |
| 6,346,102 B1 | 2/2002 | Harrington et al. | |
| 6,712,810 B2 | 3/2004 | Harrington et al. | |
| 6,726,682 B2 | 4/2004 | Harrington et al. | |
| 6,780,182 B2 | 8/2004 | Bowman et al. | |
| 7,220,259 B2 | 5/2007 | Harrington et al. | |

(Continued)

*Primary Examiner* — Patricia Bianco
*Assistant Examiner* — Nihir Patel
(74) *Attorney, Agent, or Firm* — Vista IP Law Group LLP

(57) ABSTRACT

Medical devices and related methods are disclosed for delivering an implant into the body of a patient. The devices include a damping assembly having an internal chamber with a varying inner diameter, and a piston slideably disposed therein. The piston is operably connected with a catheter portion such that movement of the piston is associated with concurrent movement of the catheter for implant delivery. The varying inner diameter of the damping assembly results in a decrease in damping force during implant delivery, thus providing a substantially constant velocity of implant delivery.

17 Claims, 3 Drawing Sheets

U.S. PATENT DOCUMENTS 7,582,085 B2    9/2009   Bowman et al.
8,292,947 B2 * 10/2012   Hornig ........................ 623/1.21
2004/0255958 A1 12/2004 Harrington et al.
2006/0107956 A1 * 5/2006 Hendricksen et al. ... 128/205.24
2007/0215163 A1   9/2007 Harrington et al.
2009/0036840 A1 * 2/2009 Viray et al. .................. 604/264

* cited by examiner

CONSTANT RATE DELIVERY DEVICE

FIELD OF THE INVENTION

The present invention provides medical devices and associated methods for the delivery of one or more implants into the body of a patient.

BACKGROUND

Current female sterilization procedures often make use of implants that are placed within the fallopian tubes. For example, the Adiana® Permanent Contraception procedure (Hologic, Inc., Marlborough, Mass.) is a minimally invasive procedure in which a delivery catheter is passed through the vagina and cervix and into the uterus. A low level of radiofrequency energy is delivered to a small section of each fallopian tube to create a superficial lesion. A small implant is then placed within each fallopian tube at the location where the lesions were created. Over a period of time, tissue grows into and/or around the implants leading to complete occlusion of the fallopian tubes to thereby provide the desired sterilization. Such implants and procedures are described, for example, in U.S. Pat. No. 7,220,259, which is incorporated herein by reference.

Implants are placed within the fallopian tubes using minimally-invasive devices such as delivery catheters designed to be inserted into the patient's uterus and into the fallopian tubes. Such catheters are preferably inserted in conjunction with a hysteroscope to visualize implant placement. Conventional implant deployment mechanisms for tubal implants may make use of viscous-fluid damper assemblies. Such systems are used to limit the peak velocity at which the implants are delivered from the delivery catheter into the patient's body. It is often desirable, however, to deploy the implant quickly so that its position is not compromised during the delivery thereof. It is also preferred to deliver the implant at a substantially constant velocity over the entire delivery process. The use of conventional damper assemblies, while effective to prevent implant delivery at too high a velocity, may result in a delivery velocity that varies (i.e., decreases) during the delivery procedure, and a procedure time that is longer than optimal.

It is an object of the present invention to provide devices and associated methods that facilitate rapid implant deployment at a substantially constant velocity.

SUMMARY OF THE INVENTION

In one aspect, the present invention comprises medical devices used to deliver one or more implants into the body of a patient.

In another aspect, the present invention comprises a kit that includes a medical device used to deliver one or more implants into the body of a patient.

In yet another aspect, the present invention comprises a method of delivering an implant into the body of a patient, using the devices of the present invention.

In certain embodiments, the present invention comprises a medical device comprising an elongated catheter configured to house an implant intended for delivery into the body of a patient. The catheter comprises an opening configured to allow passage of the implant from the catheter into the patient. The medical device further comprises a damper body comprising an internal chamber, which includes a distal end characterized by a distal inner diameter, a proximal end characterized by a proximal inner diameter, and a distal opening in the distal end. The distal inner diameter is less than the proximal inner diameter. A piston comprising an elongated body terminating in a piston head is slideably disposed with respect to the damper body, such that the elongated body of the piston slides within the distal opening of the damper body, and the piston head slides within the internal chamber of the damper body. The piston is operably connected to the elongated catheter such that movement of the piston head towards the proximal end of the damper body is associated with concurrent movement of the elongated catheter relative to the implant such that the implant is caused to move through the opening in the elongated catheter and into the patient.

In other embodiments, the present invention comprises a method of delivering an implant into the body of a patient. The method makes use of a medical device comprising an elongated catheter configured to house an implant intended for delivery into the body of a patient. The catheter comprises an opening configured to allow passage of the implant from the catheter into the patient. The medical device further comprises a damper body comprising an internal chamber, which includes a distal end characterized by a distal inner diameter, a proximal end characterized by a proximal inner diameter, and a distal opening in the distal end. In all embodiments, the distal inner diameter is less than the proximal inner diameter. A piston comprising an elongated body terminating in a piston head is slideably disposed with respect to the damper body, such that the elongated body of the piston slides within the distal opening of the damper body, and the piston head slides within the internal chamber of the damper body. The piston is operably connected to the elongated catheter such that movement of the piston head towards the proximal end of the damper body is associated with concurrent movement of the elongated catheter relative to the implant such that the implant is caused to move through the opening in the elongated catheter and into the patient. The device includes an actuator, that when actuated in accordance with the method of the present invention, results in the movement of the piston and the delivery of the implant from the catheter into the patient.

DESCRIPTION OF THE PREFERRED EMBODIMENTS

The present invention provides devices and methods used to deliver one or more implants into the body of a patient. Use of the present invention results in the delivery of implants at a more constant velocity and force when compared with prior art devices and methods, thus yielding enhanced control over the delivery device and a decreased risk of improper implant placement. Although the present invention is described with specific reference to the placement of sterilization implants within fallopian tubes, it should be recognized that the devices and methods of the present invention are equally applicable to the delivery of other medical implants into the body, such as into a blood vessel, urethra, ureter, or other lumens or spaces within the cardiovascular, urogenital, or gastrointestinal systems.

Figure 1:
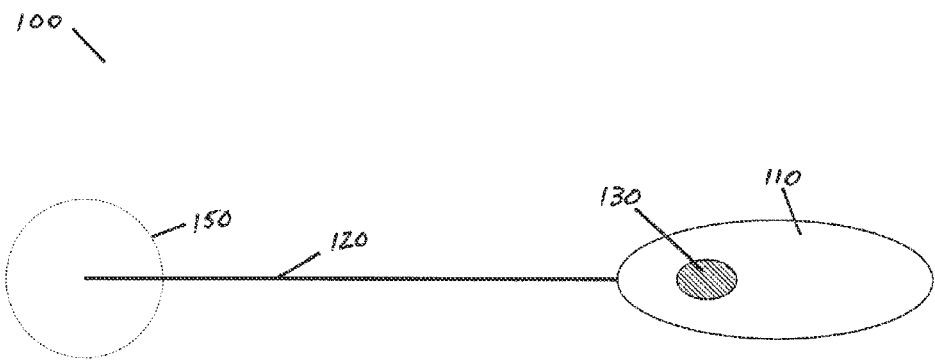
FIG. 1 is a top view of an implant delivery device, according to an embodiment of the present invention.

An embodiment of a medical device in accordance with the present invention is shown in FIG. 1. Device 100 includes a handle 110, a catheter portion 120, and an actuator 130. The catheter includes a distal portion 150. In an exemplary embodiment, the catheter portion 120 of device 100 is inserted into the patient's body with the use of a hysteroscope such that the distal portion 150 is placed within a fallopian tube of a patient. Handle 110 remains outside of the patient so that a physician or other health care provider may actuate the actuator 130 to deploy an implant housed within the catheter 120 into the fallopian tube.

Figure 2:
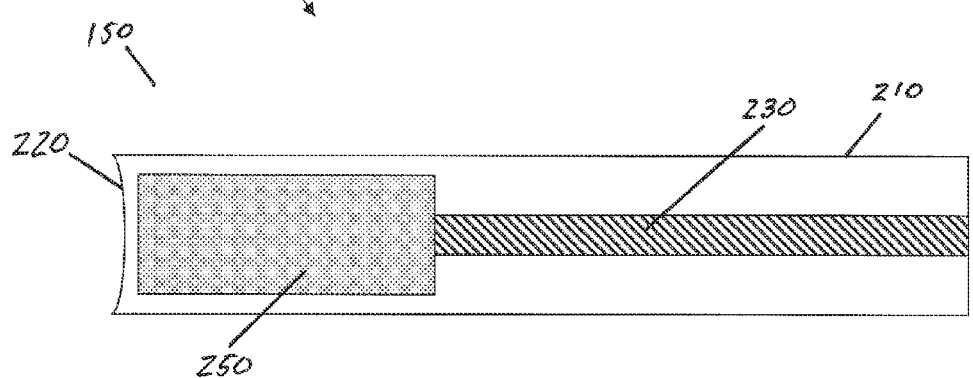
FIG. 2 is a cross-sectional view of a distal portion of an implant delivery device, according to an embodiment of the present invention.

A close-up, cross-sectional view of distal portion 150 of catheter 120 is shown in FIG. 2. Catheter 120 is preferably a cylindrical tube with an outer wall 210 terminating in a distal opening 220. Although the distal opening 220 is shown at the distal end or tip of the catheter 120 in the embodiment shown in FIG. 2, in other embodiments the distal opening 220 is located in the outer wall 210 near the distal end thereof. Housed within the distal portion 150 of catheter 120 is an implant 250 that, according to an exemplary embodiment, is intended for placement within a patient's fallopian tube during a sterilization procedure. In a preferred embodiment, implant 250 is held relatively stationary by push rod 230 while the outer wall or sheath 210 is retracted or otherwise withdrawn proximally towards handle 110 to "reveal" the implant 250 from the distal opening 220 and deliver it into a desired location within the patient's body. In another embodiment, the implant 250 is simply pushed by push rod 230 through the distal opening 220 for delivery thereof.

Figure 3:
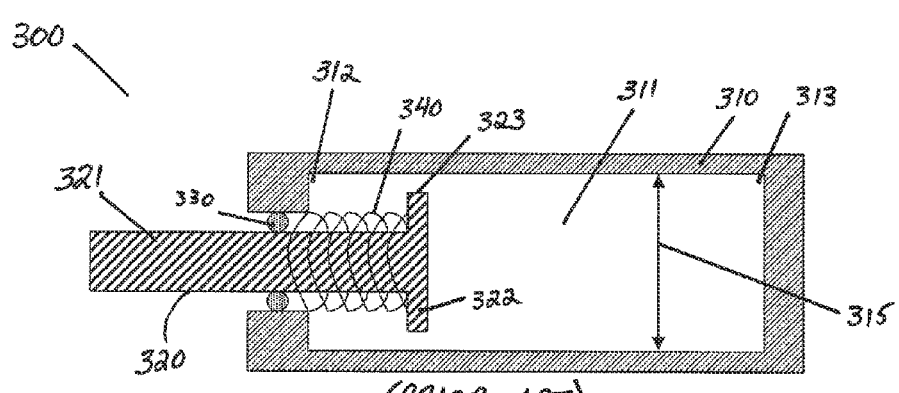
FIG. 3 is a cross-sectional view of a damper assembly according to the prior art.

The device 100 includes a damper assembly, a prior art embodiment of which is shown in FIG. 3. Prior art damper assembly 300 includes a damper body 310 having a cylindrical internal chamber 311 having a distal end 312 and a proximal end 313. The inner diameter 315 of the internal chamber 311 is substantially constant between the distal end 312 and the proximal end 313. A viscous fluid is kept within the internal chamber 311 with o-ring seals 330. A piston 320, having an elongated body 321 and a piston head 322, is operably connected to the catheter 120 and slidably positioned within the internal chamber 311. The piston 320 is biased to move from a retracted position to an extended position by spring 340. During use, the piston 320 is retained in a retracted position by any suitable mechanism, such as, for example, by a button-actuated latch mechanism (as is known in the art), until such time as the catheter is placed at a desired location for implant delivery. When the catheter is so placed, the operator actuates the actuator 130, which releases the piston 320 from the retracted position so that the piston 320 is free to move towards its biased position. Such movement results in the piston head 322 moving towards the proximal end 313 of the internal chamber 311, and the concurrent withdrawal of the catheter outer wall such that the implant 250 is revealed and placed at a desired location within the patient.

One possible limitation of the prior art damper assembly 300, however, is that the velocity at which the implant 250 is delivered from the catheter 120 may vary. Such variability is attributable to the decrease in force applied to the piston head 322 by the spring 340 as it moves the piston 320 from the retracted position to the extended position. The velocity at which the implant 250 is delivered from the catheter 120 likewise decreases as the implant 250 is revealed from the catheter 120, thus increasing procedure time and the possibility for device movement during implant deployment.

Figure 4:
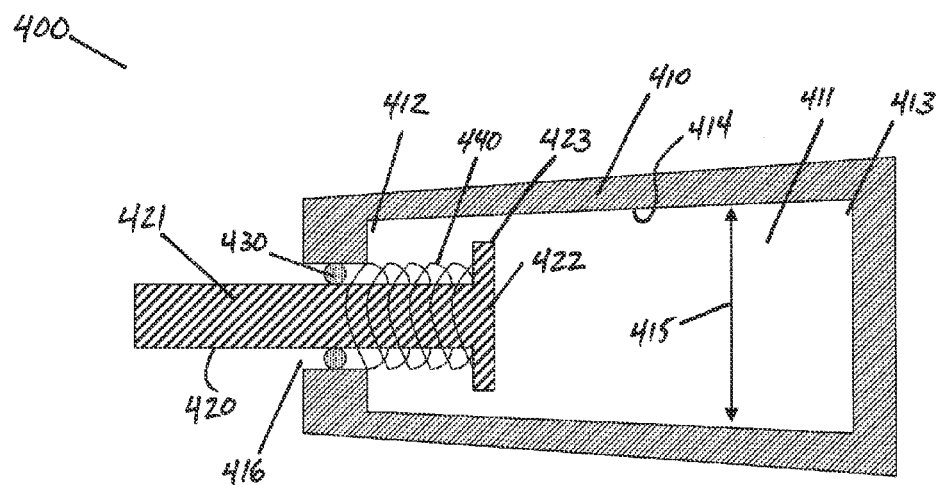
FIG. 4 is a cross-sectional view of a damper assembly, in accordance with an embodiment of the present invention.

In one embodiment, the medical device of the present invention includes a damper assembly 400 as shown in FIG. 4. Damper assembly 400 includes a damper body 410 having an internal chamber 411 having a distal end 412 and a proximal end 413. The inner diameter 415 of the internal chamber 411 is smaller at the distal end 412 than at the proximal end 413. A viscous fluid is kept within the internal chamber 411 with o-ring seals 430. A piston 420, having an elongated body 421 and a piston head 422, is operably connected to the catheter 120 or a portion thereof, and slidably positioned through distal opening 416 and within the internal chamber 411. The piston 420 is biased to move from a retracted position to an extended position by any suitable bias means, such as spring 440. During use, the piston 420 is retained in a retracted position by any suitable mechanism, such as, for example, by a button-actuated latch mechanism (as is known in the art), until such time as the catheter is placed at a desired location for implant delivery. When the catheter is so placed, the operator actuates an actuator 130, which releases the piston 420 from the retracted position so that the piston 420 is free to move towards its biased position. Such movement results in the piston head 422 moving towards the proximal end 413 of the internal chamber 411, and the concurrent withdrawal of the catheter outer wall or sheath such that the implant 250 is revealed and placed at a desired location within the patient.

Because the inner diameter 415 of the internal chamber 411 is smaller at the distal end 412 than the proximal end 413, the damping force applied against the piston head 422 decreases as it moves from the retracted position to the extended position. Without wishing to be bound by theory, the reduction in damping force is at least partially due to the increased distance between the outer edge 423 of the piston head 422, and the internal wall 414 of the internal chamber 411, as the piston head 422 moves through the viscous fluid within the internal chamber 411 from a retracted position to an extended position, and therefore towards the proximal end 413 of the internal chamber 411. When compared with the prior art damping assembly 300, the damping assembly 400 of the present invention will deliver the implant from the catheter 120 at a more constant velocity because the decrease in damping force counteracts the decrease in the force applied by the bias means (for example, spring 440) as it unstresses and moves the piston from a retracted position to an extended position. The piston 420 therefore moves from the retracted position to the extended position without a significant reduction in velocity.

In a preferred embodiment, the inner diameter 415 of the internal chamber 411 is 1% to 5% larger at the proximal end 413 than at the distal end 412, and more preferably 2% to 3%. In one example, the inner diameter 415 is 0.327 inches/at the proximal end 413 and 0.336 inches at the distal end 412, which represents a difference of 2.75%. Also preferred is that the distance between the outer edge 423 of the piston head 422 and the internal wall 414 of the internal chamber 411 increases by about 75% to about 150% as the piston head 422 moves from a retracted position to an extended position. In one example, the distance between the outer edge 423 of the piston head 422 and the internal wall 414 of the internal chamber 411 is 0.005 to 0.015 inches, and preferably about 0.010 inches, in the retracted position and 0.015 to 0.025 inches, and preferably about 0.020 inches, in the extended position.

In a preferred embodiment, the velocity of the piston 420 as it moves from its retracted position to its extended position is less than about 0.10 inches per second. More preferably, the velocity of the piston 420 remains within the range of 0.05 to 0.10 inches per second over the entire "stroke" of movement between the retracted position to the extended position. Also preferred is that this stroke of movement, and thus the delivery of the implant, take 0.5 to 4.3 seconds to complete. As used herein, "retracted position" is intended to mean the position of the piston 420 as held within the device 100 prior to the implant 250 being delivered into a patient's body, and "extended position" is intended to mean the position of the piston 420 after it completes its movement after being released from the retracted position and acted upon by a bias means, such as spring 440. In accordance with the present invention, the velocity of the piston between the retracted and extended positions is substantially constant, preferably not varying by more than 0.025 inches per second. While the piston head 422 will move towards the proximal end 413 of internal chamber 411 during movement of the piston 420 from the retracted position to the extended position, it is not necessary that the piston head 422 make contact with the proximal end 413. In all embodiments of the present invention, the inner diameter 415 of the internal chamber 411 is smaller at the location of the piston head 422 in its retracted position than the location of the piston head 422 in its extended position.

The bias means used in the present invention urges the piston 420 from the retracted position to the extended position. In a preferred embodiment, as shown in FIG. 4, the bias means is a spring 440 positioned within the damper body 410 between the distal end 412 of the internal chamber 412 and the piston head 423. In other embodiments, the bias means is a spring in operable connection to the piston but located outside of the damper body 410. In a preferred embodiment, the bias means provides a spring force of between 5 lb·f and 10 lb·f.

Figure 5:
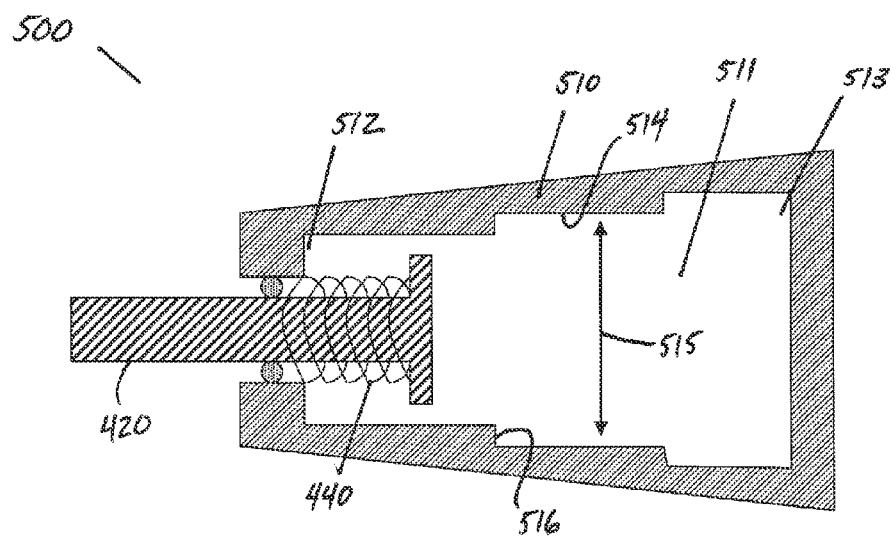
FIG. 5 is a cross-sectional view of a damper assembly, in accordance with an embodiment of the present invention.

In the preferred embodiment shown in FIG. 4, the inner diameter 415 of the internal chamber 411 tapers at a constant angle between distal end 412 and proximal end 413. In other embodiments, the change in the internal diameter 415 is non-uniform. For example, in the embodiment shown in FIG. 5, the damper body 510 includes an internal wall 514 of internal chamber 511 that includes one or more steps or jogs 516. As such, the increase in the inner diameter 515 of the internal chamber from distal end 512 to proximal end 513 occurs in a stepped fashion rather than as a gradual, continuous change. In other embodiments, the inner diameter tapers by more than one angle over the length of the internal chamber.

The viscous fluid within the internal chamber 411 of the damper body 410 is any suitable viscous fluid or semi-solid material, such as silicone. In a preferred embodiment, the viscous fluid has a viscosity of about 10,000 centiStokes.

The piston 420 is operably connected to the catheter 120 by any suitable mechanism that translates movement of the piston into movement of the catheter. In one non-limiting example, a latch is used to keep the piston 420 in a retracted position until the actuator 130 is depressed, whereupon the latch is moved into a position that allows for movement of the piston to the extended position. Such a latch system is known in the art, and is used, for example, in the current Adiana® Permanent Contraception delivery device.

The portions of the damper assembly 400, including the damper body 410 and the piston 420 are made from any suitable materials using known fabrication techniques. In a preferred embodiment, the damper body 410 and piston 420 comprise aluminum, stainless steel, and/or acetal plastic and are machined to specifications.

The present invention is described with specific reference to an occlusive implant that is placed within the fallopian tube(s) for sterilization purposes. Related sterilizations procedures and implant delivery devices are described in: U.S. patent application Ser. No. 12/692,057, entitled "Sterilization Device and Method"; U.S. patent application Ser. No. 12/773,332, entitled "Radiopaque Implant", U.S. Patent Application Publication No. 2009-0036840, entitled "Atraumatic Ball Tip and Side Wall Opening"; U.S. Patent Application Publication Nos. 2007-0215163 and 2004-0255958, both entitled "Method and Apparatus for Tubal Occlusion"; U.S. patent application Ser. No. 11/562,882, entitled "Delivery Catheter with Implant Ejection Mechanism"; U.S. Pat. Nos. 7,582,085 and 6,780,182, both entitled "Catheter Placement Detection System and Operator Interface"; U.S. Pat. Nos. 7,220,259, 6,726,682, 6,712,810, 6,346,102, 6,309,384, 6,068,626, and 5,954,715, each entitled "Method and Apparatus for Tubal Occlusion; U.S. Pat. No. 5,681,572, entitled "Porous Material Produce and Process"; and U.S. Pat. No. 5,095,917, entitled "Transuterine Sterilization Apparatus and Method"; all of which are incorporated herein by references in their entireties as part of the present disclosure. It should be recognized, however, that the devices and methods of the present invention are equally applicable to the delivery of any implant into bodily spaces. Non-limiting examples of such implants include stents, filters, embolics, injectables, and other compressible, non-compressible, expandable, and non-expandable implants.

In a preferred embodiment, the implant 250 includes a plurality of pores and is formed as a matrix or plug having a pore size chemistry and architecture which may facilitate cellular ingrowth into the material over time. In the illustrated embodiments of the present invention, the implant body 250 is an elongate body having an approximately cylindrical configuration. However, as one skilled in the art would appreciate, the implant body 250 can take on any suitable configuration that facilitates and enables fallopian tube occlusion. In terms of dimensions, the implant body 250 may have, in one embodiment, an outer diameter ranging between about 1.0 mm and about 3.0 mm and, more preferably, may have an outer diameter ranging between about 1.4 mm and about 1.8 mm. Additionally, the implant body 250 may have, in one embodiment, an overall length ranging between about 2 mm and about 10 mm and, more preferably, may have a an overall length ranging between about 3 mm and about 6 mm.

In certain embodiments, the implant 250 is made of ePTFE (also referred to as expanded Teflon or expanded polytetraflouroethylene), porous silicone, acrylic copolymer, cellulose acetate, polyethylene and high density polyethylene (HDPE), PE, polyester, and sintered, micro-knurled, or molded titanium and platinum. Textured polyamides or polyimides, hydroxyapitite, and hydrogels are also potential suitable materials. Preferably, these materials are formed into a foamed material, which is molded or otherwise formed into the implant body. The preferable pore sizes of the foam fall into the two distinct ranges, namely a 1-20 micron pore size or a 40-200 micron pore size. The foam is preferably formed as a reticulated foam, meaning that the pores communicate with other pores, rather than existing as discrete and isolated voids within the material. In one embodiment, the implant body 250 is made from silicone foam having a pore size ranging between about 50 and about 150 microns. Silicone foam is readily formed into porous implants with the procedure set forth, for example, in U.S. Pat. No. 5,605,693, entitled "Method of Marking a Porous Implant", which is incorporated by reference in its entirety as part of the present disclosure.

Figure 6:
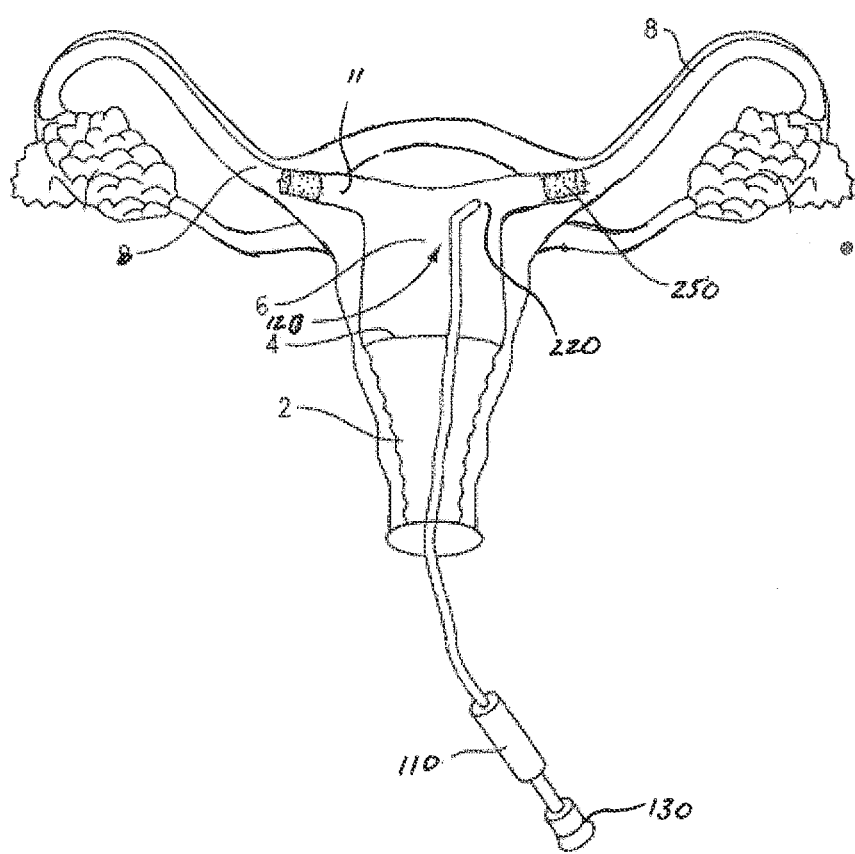
FIG. 6 is a schematic illustration of the delivery of implants into the fallopian tubes of a patient, in accordance with an embodiment of the present invention.

According to an embodiment of the present invention, an implant is delivered into the body of a patient using the device 100. One or more implants 250 are loaded into the distal portion 150 of device 100. The loaded delivery device 100 is then packaged, sterilized such as by ethylene oxide gas, and then shipped and stored until use. When ready for use, the delivery device 100 is removed from its packaging materials and, in this example, is inserted into the vagina 2, through the cervix 4, and into the uterus 6, as shown in FIG. 6. Such insertion may be done under x-ray guidance, sonographically, hysteroscopically, or in the absence of visualization, and may be conducted under general and/or local anesthesia. The distal end 220 of the catheter 120 is inserted through the uterotubal junction 11 and into the fallopian tube 8. Once at this location, the operator actuates the actuator 130 to release the implant 250 from the catheter 120. The process is preferably repeated for each fallopian tube, and may be done in conjunction with RF energy delivery to the site of implant delivery, as is known in the art.

The present invention provides for the delivery of implants into bodily spaces with advantages not heretofore known. Although the present invention is described with specific reference to an occlusive implant that is placed within the fallopian tubes for sterilization purposes, it is intended that the present invention be applicable to any implant for delivery into bodily spaces. Furthermore, it will be apparent to those skilled in the art that various modifications and variations can be made in the structure and methodology of the present invention. It is intended that the present invention cover the modifications and variations of this invention provided that they come within the scope of the appended claims and their equivalents.

I claim:

1. A medical device, comprising:
   an elongated catheter configured to house an implant intended for delivery into the body of a patient, said catheter comprising an opening to allow passage of the implant therethrough from the catheter into the patient;
   a damper body comprising an internal chamber closed at a proximal end thereof and having a distal opening in a distal end thereof, an inner diameter of the internal chamber at the distal end being less than an inner diameter of the internal chamber at the proximal end; and
   a piston comprising an elongated body terminating in a piston head, said elongated body of said piston slidably disposed within said distal opening of said damper body, said piston head slidably disposed within said internal chamber of said damper body;
   wherein said piston is operably connected to said elongated catheter such that movement of said piston head towards said proximal end of said damper body is associated with concurrent movement of said elongated catheter relative to said implant such that said implant is caused to move through said opening in said elongated catheter, and
   wherein said piston is biased to move from a retracted position to an extended position, said piston head moving closer to said proximal end of said damper body when said piston moves from said retracted position to said extended position.

2. The medical device of claim 1, wherein said piston is biased by a spring.

3. The medical device of claim 2, wherein said spring is located between said piston head and said distal end of said damper body.

4. The medical device of claim 1, further comprising a holding mechanism that holds said piston in said retracted position, and an actuator that releases said piston from said retracted position.

5. The medical device of claim 4, wherein the movement of said piston from said retracted position to said extended position upon actuation of said actuator takes between 0.5 and 4.3 seconds.

6. The medical device of claim 1, wherein said piston moves from said retracted position to said extended position at a velocity of between 0.05 to 0.10 inches per second.

7. The medical device of claim 6, wherein said velocity is substantially constant during the movement of said piston from said retracted position to said extended position.

8. The medical device of claim 1, further comprising fluid within said internal chamber.

9. The medical device of claim 8, wherein said fluid comprising silicone.

10. The medical device of claim 1, further comprising an o-ring seal within said distal opening of said damper body.

11. The medical device of claim 1, wherein an inner diameter of said internal chamber tapers at a constant angle between said distal inner diameter and said proximal inner diameter.

12. The medical device of claim 1, wherein an inner diameter of said internal chamber tapers at a varying angle between said distal inner diameter and said proximal inner diameter.

13. The medical device of claim 1, wherein an inner diameter of said internal chamber includes one or more jogs between said distal inner diameter and said proximal inner diameter.

14. The medical device of claim 1, wherein said proximal inner diameter is 1% to 5% larger than said distal inner diameter.

15. The medical device of claim 14, wherein said proximal inner diameter is 2% to 3% larger than said distal inner diameter.

16. The medical device of claim 1, wherein said damper body comprises aluminum.

17. The medical device of claim 1, wherein a clearance distance between an outer surface of said piston head and said distal inner diameter of said internal chamber is between 0.005 to 0.015 inches, and a clearance distance between an outer surface of said piston head and said proximal inner diameter of said internal chamber is between 0.015 to 0.025 inches.

* * * * *